United States Patent
Suh et al.

(10) Patent No.: US 10,730,809 B2
(45) Date of Patent: Aug. 4, 2020

(54) BUTADIENE PREPARATION METHOD PROVIDING EXCELLENT CATALYST REPRODUCIBILITY

(71) Applicant: LG CHEM, LTD., Seoul (KR)

(72) Inventors: Myung Ji Suh, Daejeon (KR); Dong Hyun Ko, Daejeon (KR); Jun Han Kang, Daejeon (KR); Kyong Yong Cha, Daejeon (KR); Ye Seul Hwang, Daejeon (KR); Jun Kyu Han, Daejeon (KR); Sang Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 69 days.

(21) Appl. No.: 16/098,077

(22) PCT Filed: Sep. 21, 2017

(86) PCT No.: PCT/KR2017/010371
§ 371 (c)(1),
(2) Date: Oct. 31, 2018

(87) PCT Pub. No.: WO2018/080025
PCT Pub. Date: May 3, 2018

(65) Prior Publication Data
US 2019/0144362 A1    May 16, 2019

(30) Foreign Application Priority Data

Oct. 28, 2016  (KR) .................. 10-2016-0142067

(51) Int. Cl.
| | | |
|---|---|---|
| C07C 5/48 | (2006.01) |
| B01J 23/86 | (2006.01) |
| B01J 23/78 | (2006.01) |
| B01J 21/06 | (2006.01) |
| B01J 23/72 | (2006.01) |
| B01J 23/76 | (2006.01) |
| B01J 23/745 | (2006.01) |
| B01J 23/847 | (2006.01) |
| B01J 23/00 | (2006.01) |
| B01J 23/80 | (2006.01) |
| B01J 37/02 | (2006.01) |
| B01J 37/03 | (2006.01) |
| B01J 37/04 | (2006.01) |
| B01J 37/06 | (2006.01) |
| B01J 37/08 | (2006.01) |

(52) U.S. Cl.
CPC .............. *C07C 5/48* (2013.01); *B01J 21/06* (2013.01); *B01J 23/005* (2013.01); *B01J 23/72* (2013.01); *B01J 23/745* (2013.01); *B01J 23/76* (2013.01); *B01J 23/78* (2013.01); *B01J 23/80* (2013.01); *B01J 23/847* (2013.01); *B01J 23/86* (2013.01); *B01J 37/0236* (2013.01); *B01J 37/031* (2013.01); *B01J 37/04* (2013.01); *B01J 37/06* (2013.01); *B01J 37/08* (2013.01); *C07C 2523/745* (2013.01)

(58) Field of Classification Search
CPC .... C07C 5/48; C07C 2523/745; B01J 23/005; B01J 23/72; B01J 23/745; B01J 23/76; B01J 23/78; B01J 23/80; B01J 23/847; B01J 23/86; B01J 21/06; B01J 37/0236; B01J 37/031; B01J 37/04; B01J 37/06; B01J 37/08
See application file for complete search history.

(56) References Cited

U.S. PATENT DOCUMENTS

| | | | |
|---|---|---|---|
| 7,282,619 B2 | 10/2007 | Kowaleski et al. | |
| 7,388,107 B2 | 6/2008 | Jinno et al. | |
| 8,513,479 B2 | 8/2013 | Chung et al. | |
| 9,346,747 B2 | 5/2016 | Tamura et al. | |
| 2008/0183024 A1* | 7/2008 | Klanner | C07C 5/3337 585/633 |
| 2014/0163288 A1 | 6/2014 | Ruttinger et al. | |
| 2016/0152532 A1 | 6/2016 | Grune et al. | |

FOREIGN PATENT DOCUMENTS

| | | |
|---|---|---|
| JP | S58-188823 | 11/1983 |
| JP | 2005314314 | 11/2005 |
| JP | 2007510534 | 4/2007 |

(Continued)

OTHER PUBLICATIONS

Jie et al., "Regeneration of sintered Rh/ZrO2 catalysts via Rh re-dispersion and Rh-ZrO2 interaction," Science China Technological Sciences 59(7): 1023-1028 (2016).

*Primary Examiner* — In Suk C Bullock
*Assistant Examiner* — Jason Y Chong
(74) *Attorney, Agent, or Firm* — Dentons US LLP

(57) ABSTRACT

A method of preparing butadiene that includes supplying butene, oxygen, nitrogen, and steam into a reactor filled with a metal oxide catalyst, and performing an oxidative dehydrogenation reaction at a temperature of 300 to 450° C. as a reaction step; after the reaction step, maintaining supplying the butene, oxygen, nitrogen, and steam within a range within which the flow rate change of the butene, oxygen, nitrogen, and steam is less than ±40%, or stopping supplying the butene, and cooling the reactor to a temperature range of 200° C. or lower and higher than 70° C. as a first cooling step; and after the first cooling step, stopping supplying the butene, oxygen, nitrogen, and steam or stopping at least supplying the butene, and cooling the reactor to a temperature of 70° C. or lower as a second cooling step.

19 Claims, No Drawings

(56) References Cited

FOREIGN PATENT DOCUMENTS

| | | |
|---|---|---|
| JP | 2010534553 | 11/2010 |
| JP | 2011001341 | 1/2011 |
| JP | 2016525518 | 8/2016 |
| KR | 10-2006-0116205 | 11/2006 |
| KR | 10-0847206 | 7/2008 |
| KR | 10-2016-0032187 | 3/2016 |
| KR | 10-2016-0063477 | 6/2016 |
| KR | 10-2016-0073300 | 6/2016 |
| WO | 2005/037738 | 4/2005 |
| WO | 2014054408 | 4/2014 |
| WO | 2015121297 | 8/2015 |

\* cited by examiner

BUTADIENE PREPARATION METHOD PROVIDING EXCELLENT CATALYST REPRODUCIBILITY

CROSS-REFERENCE TO RELATED APPLICATION

This application is a National Stage Application of International Application No. PCT/KR2017/010371 filed on Sep. 21, 2017, which claims priority to Korean Patent Application No. 10-2016-0142067, filed on Oct. 28, 2016 in the Korean Intellectual Property Office, the disclosure of which is incorporated herein by reference.

TECHNICAL FIELD

The present invention relates to a method of preparing butadiene having excellent catalyst reproducibility, and more particularly, to a method of preparing butadiene, which has excellent catalyst reproducibility and is effective in reducing operation time and cost by preventing catalyst deactivation which may occur when oxidative dehydrogenation reaction is stopped as needed and then restarted.

BACKGROUND ART

Butadiene is an important basic chemical substance and is used as an intermediate for numerous petrochemicals such as synthetic rubber and electronic materials. In addition, butadiene is the most important basic fraction in the petrochemical market, and demand and value thereof are gradually increasing. Examples of butadiene preparation methods include naphtha cracking, direct dehydrogenation of normal-butene (n-butene), and oxidative dehydrogenation of normal-butene (n-butene).

Thereamong, oxidative dehydrogenation of butene is a reaction, in which butene and oxygen react with each other in the presence of a metal oxide catalyst to produce 1,3-butadiene and water. Since the produced water is stable, the reaction is thermodynamically very advantageous. In addition, since oxidative dehydrogenation of butene is an exothermic reaction unlike direct dehydrogenation of butene, 1,3-butadiene may be generated in a high yield even at a low reaction temperature as compared with direct dehydrogenation of butene, and additional heat supply is not required. Thus, oxidative dehydrogenation of butene may be an effective production process to meet demand for 1,3-butadiene.

However, in an oxidative dehydrogenation reactor system, it is often necessary to stop operation of a reaction process for various reasons. When the operation is stopped and then restarted, a catalyst is reused, in which case reproducibility of catalyst activity should be ensured to reduce cost and time.

Therefore, there is a need for a method that can reproduce the existing catalytic activity when reaction is terminated and then restarted.

PRIOR ART DOCUMENT

[Patent Document] (Patent Document 1) KR Patent No. 10-0847206 (B1)

DISCLOSURE

Technical Problem

Therefore, the present invention has been made in view of the above problems, and it is one object of the present invention to provide a method of preparing butadiene, which has excellent catalyst reproducibility and reduces operation time and cost by preventing catalyst deactivation which may occur when oxidative dehydrogenation reaction is stopped as needed and then restarted.

The above objects and other objects of the present invention can be achieved by the present invention described below.

Technical Solution

In accordance with one aspect of the present invention, provided is a method of preparing butadiene having excellent catalyst reproducibility, including a reaction step of introducing a reactant containing butene, oxygen, nitrogen, and steam as constituents into a reactor filled with a metal oxide catalyst, and performing oxidative dehydrogenation reaction at a temperature of 300 to 450° C.; a first cooling step of, after the reaction step, maintaining supply of the reactant within a range within which the flow rate change rate of each of the constituents is less than ±40% or stopping supply of the butene contained in the reactant, and cooling the reactor to a temperature range of 200° C. or lower and higher than 70° C.; and a second cooling step of, after the first cooling step, stopping supply of the reactant or stopping at least supply of the butene contained in the reactant, and cooling the reactor to a temperature of 70° C. or lower.

Advantageous Effects

As apparent from the foregoing, the present invention advantageously provides a method of preparing butadiene, which is effective in reducing operation time and cost by preventing catalyst deactivation which may occur when oxidative dehydrogenation reaction is stopped as needed and then restarted.

BEST MODE

Hereinafter, the method of preparing butadiene having excellent catalyst reproducibility according to the present invention will be described in detail.

The present inventors have conducted studies on the reaction activity of a catalyst when a reaction was stopped by various methods during a reaction process for preparing butadiene and then restarted. Through this study, it was confirmed that catalyst deactivation may be prevented in the case where supply of all or a part of reactants was maintained while cooling to a predetermined temperature range, and the present invention was completed based on this finding.

The method of preparing butadiene having excellent catalyst reproducibility according to the present invention will be described in detail as follows.

The method of preparing butadiene having excellent catalyst reproducibility according to the present invention includes a reaction step of introducing a reactant containing butene, oxygen, nitrogen, and steam as constituents into a reactor filled with a metal oxide catalyst, and performing oxidative dehydrogenation reaction at a temperature of 300 to 450° C.; a first cooling step of, after the reaction step, maintaining supply of the reactant within a range within which the flow rate change rate of each of the constituents is less than ±40% or stopping supply of the butene contained in the reactant, and cooling the reactor to a temperature range of 200° C. or lower and higher than 70° C.; and a second cooling step of, after the first cooling step, stopping supply of the reactant or stopping at least supply of the butene contained in the reactant, and cooling the reactor to a temperature of 70° C. or lower.

For example, the butene may be one or more selected from the group consisting of 1-butene, trans-2-butene, and cis-2-butene.

For example, the purity of the butene may be 95% or more, 98% or more, or 99% or more.

The reactor used for the oxidative dehydrogenation reaction is not particularly limited so long as it is a reactor generally used in the art. For example, the reactor may be a tubular reactor, a stirred-tank reactor, a fluidized-bed reactor, or a fixed-bed reactor.

For example, the fixed-bed reactor may be a multi-tubular reactor or a plate-type reactor.

For example, the reactor may be installed in an electric furnace, and, in the reactor, a reaction temperature in a catalyst layer may be kept constant, and oxidative dehydrogenation reaction may proceed while reactants continuously pass through the catalyst layer.

For example, in the first cooling step, the reactor may be cooled to a temperature of 200 to 100° C., 200 to 150° C., or 200 to 180° C. Within this range, catalyst reproducibility is excellent.

For example, in the first cooling step, the flow rate change rate may be within a range of less than ±40%, ±30% or less, or ±10% or less. Within this range, catalyst reproducibility is excellent.

The flow rate change rate is calculated by Equation 1 below.

[(flow rate in reaction step−flow rate in first cooling step)/(flow rate in reaction step)]×100    [Equation 1]

For example, in the first cooling step, the reactor may be cooled to a temperature of 200 to 100° C. while supply of the reactant is maintained.

As another example, in the first cooling step, the reactor may be cooled while supply of butene is stopped and supply of oxygen, nitrogen, and steam is maintained.

For example, in the second cooling step, the reactor may be cooled to a temperature of 70° C. or lower, 70 to 30° C., 70 to 40° C., or 70 to 60° C. while supply of the reactant is stopped or at least supply of the butene contained in the reactant is stopped. Within this range, catalyst reproducibility is excellent.

For example, in the second cooling step, supply of the butene contained in the reactant may be stopped.

For example, in the second cooling step, supply of the butene and steam contained in the reactant may be stopped.

For example, in the second cooling step, supply of all of the reactants may be stopped.

For example, the metal oxide catalyst may include iron (Fe); and at least one metal (A) selected from Cu, Ti, V, Cr, K, Al, Zr, Cs, Zn, Mg, Mn, and Co.

For example, the metal oxide catalyst may be prepared by the following steps:

a first step of preparing an aqueous solution of iron-metal precursors by dissolving a trivalent cationic iron (Fe) precursor and a cationic metal (A) precursor in distilled water; a second step of reacting the aqueous solution of iron-metal precursors with aqueous ammonia in a coprecipitation tank to form an iron-metal oxide and filtering the iron-metal oxide to obtain a slurry of the iron-metal oxide; and a third step of heating the slurry of the iron-metal oxide.

In the first step, the trivalent cationic iron (Fe) precursor and the cationic metal (A) precursor are not particularly limited so long as the precursors are commonly used in the art, and may be, for example, metal salts including a trivalent cationic iron (Fe) component and a cationic metal (A) component, respectively. As a specific example, the precursor may be a nitrate, an ammonium salt, a sulfate or a chloride of the metal component, preferably a chloride or a nitrate.

For example, the cationic metal (A) is one or more selected from the group consisting of cationic metals, and, as a specific example, may be one or more selected from the group consisting of copper (Cu), titanium (Ti), barium (V), chromium (Cr), potassium (K), aluminum (Al), zirconium (Zr), cesium (Cs), calcium (Ca), beryllium (Be), zinc (Zn), magnesium (Mg), manganese (Mn), and cobalt (Co), and preferably one or more selected from the group consisting of zinc (Zn), magnesium (Mg), manganese (Mn), and cobalt (Co), and more preferably zinc (Zn) or manganese (Mn).

For example, the trivalent cationic iron (Fe) precursor and the cationic metal (A) precursor may be included in an atomic ratio (measured according to Fe/A, EDS elemental analysis) of 1.5 to 10, 1.5 to 6, 1.5 to 5, or 1.5 to 3 to the precursor aqueous solution.

In the second step, the weight % concentration of aqueous ammonia may be, for example, 5 to 40%, 8 to 30% or around 10%. Process efficiency may be improved when aqueous ammonia within the concentration range is applied to the oxidative dehydrogenation reaction of butadiene.

In the third step, heating of the iron-metal oxide slurry may be, for example, performed in two steps of drying and sintering.

For example, the drying may be performed at 60 to 150° C., 70 to 120° C., or 80 to 100° C. for 12 to 20 hours, 14 to 20 hours, or 14 to 18 hours using a conventional drier.

For example, when sintering is performed, a conventional sintering furnace is used, and temperature is raised at a rate of temperature rise of 1 to 5° C. per minute in an air atmosphere, and a temperature of 300 to 1000° C., 400 to 700° C., or 550 to 700° C. is maintained for 2 to 20 hours, 3 to 10 hours, or 5 to 8 hours.

For example, the atomic ratio of iron (Fe) to metal (A) in the metal oxide catalyst may be from 1.5:1 to 4:1. Within this range, catalyst reproducibility is excellent.

For example, the atomic ratio of iron (Fe) to metal (A) may be 1.5:1 to 4:1, preferably 2:1 to 3:1. Within this range, when the catalyst is applied to the oxidative dehydrogenation reaction of butadiene, butadiene yield is excellent.

For example, the metal oxide catalyst may contain more than 92% by weight and 99.9% by weight or less of a spinel ferrite ($AFe_2O_4$) and 0.1% by weight or more and less than 8% by weight of an alpha ferrite ($\alpha\text{-}Fe_2O_3$), or 96 to 99.9% by weight of a spinel ferrite and 0.1 to 4% by weight of an alpha ferrite ($\alpha\text{-}Fe_2O_3$).

For example, the introduced reactant may include butene:oxygen:nitrogen:steam in a molar ratio of 1:0.1 to 2:1 to 10:1 to 30.

Specifically, the reactant may include butene:oxygen:nitrogen:steam in a molar ratio of 1:0.5 to 1:1 to 5:5 to 15 or 1:0.7 to 1.5:4 to 10:5 to 20. Within this range, operation stability and selectivity are excellent.

For example, in the oxidative dehydrogenation reaction, gas hourly space velocity (GHSV) may be 20 to 150 $h^{-1}$ based on butene.

Specifically, the gas hourly space velocity (GHSV) may be 30 to 140 $h^{-1}$ or 50 to 120 $h^{-1}$ based on butene. Within this range, a conversion rate and selectivity are increased.

For example, in the oxidative dehydrogenation reaction, a reaction temperature may be 300 to 450° C.

Specifically, the reaction temperature may be 400 to 320° C. or 320 to 380° C.

Although a method of performing the oxidative dehydrogenation reaction is not limited, the method according to the present invention is economical and excellent in energy efficiency because a separate cooling treatment is not required.

When a separate cooling treatment is performed as required, any method may be used as a method of performing the oxidative dehydrogenation reaction without particular limitation, so long as it is a method commonly used in the art.

For example, the cooling rate does not exceed 150° C. per hour or 2.5° C. per minute, preferably 100° C. per hour or 1.7° C. per minute, more preferably 50° C. per hour or 1° C. per minute, based on the temperature change of the reactor. Within this range, the catalyst reproducibility is excellent.

The method may further include a step of restarting supply of the reactant and then performing oxidative dehydrogenation reaction again at a temperature of 300 to 450° C., after the second cooling step.

For example, in the method of preparing butadiene, an activity reduction rate may be −1% or more, −0.6% or more, or 0.0% or more.

Hereinafter, the present disclosure will be described in more detail with reference to the following preferred examples. However, these examples are provided for illustrative purposes only and should not be construed as limiting the scope and spirit of the present disclosure. In addition, it will be apparent to those skilled in the art that various changes and modifications may be made without departing from the spirit and scope of the present disclosure, and such changes and modifications are also within the scope of the appended claims.

Preparation Example

<Preparation of Catalyst for Oxidative Dehydrogenation Reaction>

As a first step, 12.0 g of zinc chloride ($ZnCl_2$) and 47.7 g of ferric chloride ($FeCl_3$) were dissolved in 835.5 ml of distilled water to prepare 895.2 g of an aqueous solution of iron-metal precursors. In this case, the atomic ratio of iron (Fe) to zinc (Zn) included in the aqueous solution of iron-metal precursors is 2:1.

As a second step, an outlet for discharging an aqueous solution of iron-metal precursors and an outlet for discharging aqueous ammonia were separately installed in a coprecipitation tank filled with 8,500 ml of aqueous ammonia having pH 8 to 9. The aqueous solution of iron-metal precursors was dripped through the outlet for discharging an aqueous solution of iron-metal precursors, and at the same time, 9% aqueous ammonia was dripped through the outlet for discharging aqueous ammonia for 20 minutes while the pH of the coprecipitation tank was kept at 8 to 9.

After addition of the metal precursor aqueous solution was completed, the obtained iron-metal oxide solution was stirred for 1 hour using a stirring stirrer so that a reaction (coprecipitation) was sufficiently performed.

After completion of stirring, the solution was left at room temperature for 1 hour to precipitate all of precipitates and separate the phases. Thereafter, the coprecipitation solution was subjected to filtration under reduced pressure using a vacuum filter and washed with 5 L of distilled water so that no chloride ions remained, thereby obtaining an iron-metal oxide slurry.

As a third step, the iron-metal oxide slurry was dried at 90° C. for 16 hours for solidification, the dried solid was heated at a rate of 1° C. per minute in a sintering furnace under an air atmosphere, and a heat treatment was performed at a temperature of 650° C. for 6 hours to prepare a zinc ferrite catalyst.

It was confirmed by X-ray diffraction analysis (XRD) that the prepared zinc ferrite catalyst was composed of 98% by weight or more of a spinel ferrite and 2% by weight or less of an alpha ferrite ($\alpha$-$Fe_2O_3$).

<Preparation of Butadiene>

A mixture of 1-butene, trans-2-butene, and cis-2-butene and oxygen were used as reactants, and nitrogen and steam were additionally introduced. As a reactor, a metal tubular reactor was used.

The obtained catalyst was packed in a fixed bed reactor, and the volume of the catalyst layer contacting the reactants was fixed at 10 cc. Water was injected for steam generation, and water was vaporized at 350° C. using a vaporizer. The generated steam was mixed with the reactants, the butene mixture and oxygen, and introduced into the reactor. The amount of the butene mixture was controlled using a mass flow controller for liquid, and the amount of oxygen and nitrogen was controlled using a mass flow controller for gas, and the rate of steam injection was controlled using a liquid pump.

Temperature was raised to the reaction temperature while air was supplied to the reactor at a rate of 1 L/minute, and then the reaction was performed in the order of adjusting the flow rate of oxygen and nitrogen to the reaction conditions, supplying steam, and injecting butene.

After the reaction, the composition of the product was analyzed by a gas chromatography (GC). The conversion rate (X) of trans-2-butene and cis-2-butene, 1,3-butadiene selectivity (S-BD), 1,3-butadiene yield (Y), COx selectivity (S-COx), and an activity reduction rate were calculated by Equations 1 to 5 below.

Conversion rate (%)=(mole of reacted butene/mole of supplied butene)×100 [Equation 1]

S-BD (%)=(mole of produced 1,3-butadiene/mole of reacted 2-butene)×100 [Equation 2]

Yield (%)=(mole of produced 1,3-butadiene/mole of supplied butene)×100 [Equation 3]

S-$CO_X$ (%)=(mole of produced $CO_X$/mole of reacted 2-butene)×100 [Equation 4]

Activity reduction rate (%)=(difference in the conversion rate between a catalyst in the case where reaction is stopped at least once and a catalyst in the case where reaction is not stopped/the conversion rate of a catalyst in the case where reaction is not stopped)×100 [Equation 5]

To calculate the activity reduction rate, the conversion rate of the catalyst in the case where reaction is not stopped is taken as a reference. Tables 1 and 2 below are based on the results of the catalyst in the case where reaction is not stopped.

To confirm activity reduction rates depending on various cooling conditions, oxidative dehydrogenation reaction for butadiene preparation was performed again after reaction was stopped once under different cooling conditions. The obtained results were compared with the results of the catalyst in the case where reaction was not stopped, and the comparison results are shown in Table 1.

Reaction was repeatedly stopped at the optimal cooling conditions shown in Table 1 below, and the degree of activity reduction was confirmed. The results are shown in Table 2 below.

Example 1

In <preparation of butadiene> of Preparation Example, under the conditions shown Table 1 below, supply of reactants (butene, oxygen, nitrogen, and steam) were maintained until a reaction temperature was cooled to 200° C., and then supply of butene and steam was stopped, and a reactor was cooled to a temperature of 70° C. or lower to stop the reaction. Then, butadiene preparation was performed again under the reaction conditions shown in Table 1. The re-performance of reaction was performed in the same manner as the reaction was started before the reaction was stopped.

Example 2

In <preparation of butadiene> of Preparation Example, supply of butene was stopped, and supply of oxygen, nitrogen, and steam was maintained while a reactor was cooled to a temperature of 70° C. or lower to stop the reaction. Then, butadiene preparation was performed again under the reaction conditions shown in Table 1. The re-performance of reaction was performed in the same manner as the reaction was started before the reaction was stopped.

Comparative Example 1

Except that supply of oxygen was stopped in addition to butene, reaction was stopped and butadiene preparation was performed again in the same manner as in Example 2.

Comparative Example 2

Except that supply of steam was stopped in addition to butene, reaction was stopped and butadiene preparation was performed again in the same manner as in Example 2.

Comparative Example 3

Except that supply of steam was stopped in addition to butene and the flow rate of supplied oxygen and nitrogen was increased 2.5 times, reaction was stopped and butadiene preparation was performed again in the same manner as in Example 2.

Comparative Example 4

Except that the flow rate of supplied steam was reduced to 40%, reaction was stopped and butadiene preparation was performed again in the same manner as in Example 2.

Example 3

In <preparation of butadiene> of Preparation Example, under the conditions shown in Table 1 below, supply of reactants (butene, oxygen, nitrogen, and steam) was maintained until a reaction temperature was cooled to 200° C., and then supply of the reactants was stopped, and a reactor was cooled to 70° C. or lower to stop the reaction. Then, butadiene preparation was performed again under the reaction conditions shown in Table 1. The re-performance of reaction was performed in the same manner as the reaction was started before the reaction was stopped.

Comparative Example 5

Except that supply of butene and steam was stopped until a reaction temperature was cooled to 200° C. and the flow rate of supplied oxygen and nitrogen was increased 2.5 times, reaction was stopped and butadiene preparation was performed again in the same manner as in Example 3.

Comparative Example 6

Except that supply of butene and oxygen was stopped until a reaction temperature was cooled to 200° C., reaction was stopped and butadiene preparation was performed again in the same manner as in Example 3.

Comparative Example 7

Except that the flow rate of supplied steam was reduced to 40% until a reaction temperature was cooled to 200° C., reaction was stopped and butadiene preparation was performed again in the same manner as in Example 3.

Comparative Example 8

Except that supply of steam and oxygen was stopped in addition to butene until a reaction temperature was cooled to 200° C., and the flow rate of supplied nitrogen was increased 2.5 times, reaction was stopped and butadiene preparation was performed again in the same manner as in Example 3.

TABLE 1

| | Reaction conditions | | | | Results from experiment in which reaction was performed again after reaction was stopped | | | | | |
|---|---|---|---|---|---|---|---|---|---|---|
| Classification | Reaction temperature (° C.) | GHSV ($h^{-1}$) | Molar ratio of oxygen to 1 mole of butene | Molar ratio of steam to 1 mole of butene | Molar ratio of nitrogen to 1 mole of butene | X (%) | S-BD (%) | Y (%) | S_Cox (%) | Activity reduction rate (%) | Temperature of catalyst layer (° C.) |
| Standard (0 times) | 340 | 112 | 0.75 | 5 | 4 | 66.6 | 87.7 | 58.4 | 10.8 | — | 443 |
| Example 1 | | | | | | 67.2 | 87.4 | 58.7 | 10.9 | 0.9 | 445 |
| Example 2 | | | | | | 66.2 | 87.6 | 58.0 | 11.0 | −0.6 | 446 |
| Comparative Example 1 | | | | | | 65.6 | 87.6 | 57.4 | 11.0 | −1.5 | 444 |
| Comparative Example 2 | | | | | | 65.0 | 87.2 | 56.6 | 11.4 | −2.4 | 443 |

TABLE 1-continued

| Classification | Reaction conditions | | | | | Results from experiment in which reaction was performed again after reaction was stopped | | | | |
|---|---|---|---|---|---|---|---|---|---|---|
| | Reaction temperature (° C.) | GHSV (h⁻¹) | Molar ratio of oxygen to 1 mole of butene | Molar ratio of steam to 1 mole of butene | Molar ratio of nitrogen to 1 mole of butene | X (%) | S-BD (%) | Y (%) | S_Cox (%) | Activity reduction rate (%) | Temperature of catalyst layer (° C.) |

| Classification | Reaction temperature (° C.) | GHSV (h⁻¹) | oxygen | steam | nitrogen | X (%) | S-BD (%) | Y (%) | S_Cox (%) | Activity reduction rate (%) | Temp. of catalyst layer (° C.) |
|---|---|---|---|---|---|---|---|---|---|---|---|
| Comparative Example 3 | | | | | | 65.4 | 87.5 | 57.2 | 11.1 | −1.8 | 446 |
| Comparative Example 4 | | | | | | 64.5 | 86.8 | 55.9 | 11.6 | −3.2 | 445 |
| Standard (0 times) | 320 | 56 | 0.75 | 15 | 4 | 60.4 | 90.6 | 54.7 | 7.8 | — | 366 |
| Example 3 | | | | | | 59.8 | 90.9 | 54.4 | 7.2 | −1.0 | 368 |
| Comparative Example 5 | | | | | | 57.0 | 90.9 | 51.8 | 7.3 | −5.6 | 366 |
| Comparative Example 6 | | | | | | 59.3 | 90.9 | 53.9 | 7.2 | −1.8 | 368 |
| Comparative Example 7 | | | | | | 51.8 | 90.7 | 47.0 | 7.2 | −14.2 | 363 |
| Comparative Example 8 | | | | | | 54.4 | 90.0 | 49.0 | 5.8 | −9.9 | 361 |

As shown in Table 1, in the cases of Examples 1 to 3, compared to Comparative Examples 1 to 8, the conversion rate, yield, and selectivity respectively showed a small difference from the reference values, and the activity reduction rate was −1% or more.

Example 4

Under the reaction conditions shown in Table 2, in the same manner as in Example 1, supply of reactants (butene, oxygen, nitrogen, and steam) was maintained until a reaction temperature was cooled to 200° C., and then supply of butene and steam was stopped, and a reactor was cooled to 70° C. or lower to stop the reaction. Then, re-performance of butadiene preparation was repeated 5 times under the reaction conditions shown in Table 2 below. The re-performance of reaction was performed in the same manner as the reaction was started before the reaction was stopped.

Example 5

In the same manner as in Example 2, supply of butene was stopped, and supply of oxygen, nitrogen, and steam was maintained while a reactor was cooled to a temperature of 70° C. or lower to stop the reaction. Then, butadiene preparation was performed again under the reaction conditions shown in Table 2 below. The re-performance of reaction was performed in the same manner as the reaction was started before the reaction was stopped. Operation of stopping reaction and restarting butadiene preparation was repeated 4 times.

TABLE 2

| Classification | Reaction conditions | | | | | | Results from experiment in which reaction was performed again after reaction was stopped | | | | | |
|---|---|---|---|---|---|---|---|---|---|---|---|---|
| | Reaction temperature (° C.) | GHSV (h⁻¹) | Molar ratio of oxygen to 1 mole of butene | Molar ratio of steam to 1 mole of butene | Molar ratio of nitrogen to 1 mole of butene | Number of times reaction was stopped | X (%) | S-BD (%) | Y (%) | S_Cox (%) | Reduction rate of catalytic activity (%) | Temperature of catalyst layer (° C.) |
| Example 4 | 340 | 112 | 0.75 | 5 | 4 | Standard (0 times) | 67.0 | 87.6 | 58.7 | 10.7 | — | 446 |
| | | | | | | 1 time | 66.7 | 87.8 | 58.6 | 10.6 | −0.4 | 444 |
| | | | | | | 2 times | 67.1 | 87.3 | 58.5 | 11.2 | 0.1 | 447 |
| | | | | | | 3 times | 67.0 | 88.0 | 58.9 | 10.5 | 0.0 | 445 |
| | | | | | | 4 times | 67.5 | 87.5 | 59.1 | 10.8 | 0.7 | 446 |
| | | | | | | 5 times | 67.0 | 87.8 | 58.8 | 10.8 | 0.0 | 449 |
| Example 5 | 340 | 56 | 1 | 5 | 4 | Standard (0 times) | 93.4 | 81.9 | 76.5 | 15.5 | — | 433 |
| | | | | | | 1 time | 93.6 | 82.2 | 76.9 | 15.6 | 0.2 | 435 |
| | | | | | | 2 times | 93.8 | 82.5 | 77.5 | 15.4 | 0.4 | 434 |
| | | | | | | 3 times | 93.6 | 83.3 | 77.9 | 14.8 | 0.2 | 429 |
| | | | | | | 4 times | 93.0 | 82.8 | 77.0 | 15.2 | −0.4 | 431 |

As in Examples 4 and 5 of Table 2, according to the cooling method of the present invention, even when butadiene preparation was repeatedly performed after the reaction was stopped, the conversion rate, yield, and selectivity respectively showed a small difference from the reference values, and the activity reduction rate was −1% or more.

The invention claimed is:

1. A method of preparing butadiene, comprising:
    supplying butene, oxygen, nitrogen, and steam to a reactor filled with a metal oxide catalyst, and performing an oxidative dehydrogenation reaction at a temperature of 300 to 450° C. as a reaction step;
    after the reaction step, reducing the temperature of the reactor via a two-step process to prevent catalyst deactivation, by either:
    1) cooling the reactor by:
        (a) maintaining supply of the butene, oxygen, nitrogen, and steam within a range within which a flow rate change of each of the butene, oxygen, nitrogen, and steam is less than ±40%, and cooling the reactor to a temperature in a range of 200° C. or lower and higher than 70° C. as a first cooling step, and
        (b) after the first cooling step, stopping supply of at least the butene, and cooling the reactor to a temperature of 70° C. or lower as a second cooling step; or
    (2) cooling the reactor by:
        (c) stopping supply of the butene while supply of the oxygen, nitrogen, and steam is maintained, and cooling the reactor to a temperature in a range of 200° C. or lower and higher than 70° C. as a first cooling step; and
        (d) after the first cooling step,
            (i) maintaining supply of the oxygen, nitrogen, and steam, and cooling the reactor to a temperature of 70° C. or lower as a second cooling step, or
            (ii) stopping supply of the oxygen, nitrogen, and/or steam, and cooling the reactor to a temperature of 70° C. or lower as a second cooling step.

2. The method according to claim 1, wherein, in the second cooling step (b), either supply of the butene and steam is stopped, or supply of the butene, oxygen, nitrogen, and steam is stopped.

3. The method according to claim 2, wherein an activity reduction rate is −1% or more.

4. The method according to claim 1, wherein, in the first cooling step, the reactor is cooled to a temperature of 200° C. to 100° C.

5. The method according to claim 1, wherein the metal oxide catalyst comprises:
    iron (Fe); and
    at least one metal (A) selected from Cu, Ti, V, Cr, K, Al, Zr, Cs, Ca, Be, Zn, Mg, Mn, and Co.

6. The method according to claim 5, wherein an atomic ratio of iron (Fe) to at least one metal (A) in the metal oxide catalyst is from 1.5:1 to 4:1.

7. The method according to claim 1, wherein a molar ratio of butene: oxygen: nitrogen: steam supplied to the reactor is 1:0.1 to 2:1 to 10:1 to 30.

8. The method according to claim 1, wherein, in the oxidative dehydrogenation reaction, gas hourly space velocity (GHSV) is 20 to 150 $h^{-1}$.

9. The method according to claim 1, wherein, in the second cooling step, the reactor is cooled to a temperature of 70 to 30° C.

10. The method according to claim 1, further comprising a step of restarting supply of the butene, oxygen, nitrogen, and steam and then performing the oxidative dehydrogenation reaction again at a temperature of 300 to 450° C., after the second cooling step.

11. The method according to claim 1, wherein an activity reduction rate is −1% or more.

12. The method according to claim 1, further comprising a step of restarting supply of the butene, oxygen, nitrogen, and steam and then performing the oxidative dehydrogenation reaction again at a temperature of 300 to 450° C., after the second cooling step, wherein an activity reduction rate is −1% or more.

13. A method of preparing butadiene, comprising:
    supplying butene, oxygen, nitrogen, and steam to a reactor filled with a metal oxide catalyst containing more than 92% by weight and 99.9 by weight or less of a spinel ferrite ($AFe_2O_4$) where A is at least one metal selected from among Cu, Ti, V, Cr, K, Al, Zr, Cs, CA, Be, Zn, Mg, Mn, and Co, and 0.1 by weight or more and less than 8% by weight of an alpha ferrite ($\alpha$-Fe2O3), and performing an oxidative dehydrogenation reaction at a temperature of 300 to 450° C. as a reaction step;
    after the reaction step, reducing the temperature of the reactor via a two-step process to prevent catalyst deactivation, by either:
    1) cooling the reactor by:
        (a) maintaining supply of the butene, oxygen, nitrogen, and steam within a range within which a flow rate change of each of the butene, oxygen, nitrogen, and steam is less than ±40%, and cooling the reactor to a temperature in a range of 200° C. or lower and higher than 70° C. as a first cooling step, and
        (b) after the first cooling step, stopping supply of at least the butene, and cooling the reactor to a temperature of 70° C. or lower as a second cooling step; or
    2) cooling the reactor by:
        (c) stopping supply of the butene while supply of the oxygen, nitrogen, and steam is maintained, and cooling the reactor to a temperature in a range of 200° C. or lower and higher than 70° C. as a first cooling step; and
        (d) after the first cooling step,
            (i) maintaining supply of the oxygen, nitrogen, and steam, and cooling the reactor to a temperature of 70° C. or lower as a second cooling step, or
            (ii) stopping supply of the oxygen, nitrogen, and/or steam, and cooling the reactor to a temperature of 70° C. or lower as a second cooling step.

14. The method according to claim 1, wherein, in the second cooling step (b), either supply of the butene and steam is stopped, or supply of the butene, oxygen, nitrogen, and steam is stopped.

15. The method according to claim 13, wherein, in the first cooling step, the reactor is cooled to a temperature of 200° C. to 100° C.

16. The method according to claim 13, wherein an atomic ratio of iron (Fe) to at least one metal (A) in the metal oxide catalyst is from 1.5:1 to 4:1.

17. The method according to claim 13, wherein a molar ratio of butene: oxygen: nitrogen: steam supplied to the reactor is 1:0.1 to 2:1 to 10:1 to 30.

18. The method according to claim 13, wherein, in the oxidative dehydrogenation reaction, gas hourly space velocity (GHSV) is 20 to 150 $h^{-1}$.

19. The method according to claim 13, wherein, in the second cooling step, the reactor is cooled to a temperature of 70 to 30° C.

\* \* \* \* \*

UNITED STATES PATENT AND TRADEMARK OFFICE
CERTIFICATE OF CORRECTION

PATENT NO. : 10,730,809 B2
APPLICATION NO. : 16/098077
DATED : August 4, 2020
INVENTOR(S) : Myung Ji Suh et al.

Page 1 of 1

It is certified that error appears in the above-identified patent and that said Letters Patent is hereby corrected as shown below:

In the Claims

At Column 12, Line 49, to Column 12, Line 52, please correct Claim 14 as follows:
14. The method according to claim 13 wherein, in the second cooling step (b), either supply of the butene and steam is stopped, or supply of the butene, oxygen, nitrogen, and steam is stopped.

Signed and Sealed this
Sixth Day of October, 2020

Andrei Iancu
*Director of the United States Patent and Trademark Office*